United States Patent
Lindemann (10) Patent No.: US 8,206,390 B2
(45) Date of Patent: Jun. 26, 2012

(54) UNI-DIRECTIONAL RATCHETING BONE PLATE ASSEMBLY

(75) Inventor: Gary S. Lindemann, Collierville, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 1198 days.

(21) Appl. No.: 11/591,698

(22) Filed: Nov. 2, 2006

(65) Prior Publication Data

US 2008/0108998 A1   May 8, 2008

(51) Int. Cl.
A61B 17/56 (2006.01)
A61B 17/66 (2006.01)
A61B 17/80 (2006.01)

(52) U.S. Cl. ............... 606/71; 606/282; 606/286

(58) Field of Classification Search .......... 606/70–71, 606/280–299
See application file for complete search history.

(56) References Cited

U.S. PATENT DOCUMENTS

| | | | |
|---|---|---|---|
| 3,604,414 A | 9/1971 | Borges | |
| 5,129,903 A | 7/1992 | Luhr et al. | |
| 5,234,431 A | 8/1993 | Keller | |
| 5,261,911 A | 11/1993 | Carl | |
| 5,549,612 A | 8/1996 | Yapp et al. | |
| 5,616,142 A * | 4/1997 | Yuan et al. | 606/71 |
| 5,672,177 A | 9/1997 | Seldin | |
| 5,827,286 A | 10/1998 | Incavo et al. | |
| 5,951,558 A | 9/1999 | Fiz | |
| 6,258,089 B1 | 7/2001 | Campbell et al. | |
| 6,306,136 B1 | 10/2001 | Baccelli | |
| 6,306,139 B1 | 10/2001 | Fuentes | |
| 6,328,738 B1 * | 12/2001 | Suddaby | 606/57 |
| 6,402,756 B1 | 6/2002 | Ralph et al. | |
| 6,413,259 B1 | 7/2002 | Lyons et al. | |
| 6,503,250 B2 | 1/2003 | Paul | |
| 6,645,208 B2 | 11/2003 | Apfelbaum et al. | |
| 6,666,867 B2 | 12/2003 | Ralph et al. | |
| 6,689,134 B2 | 2/2004 | Ralph et al. | |
| 6,695,846 B2 | 2/2004 | Richelsoph et al. | |
| 6,699,249 B2 | 3/2004 | Schlapfer et al. | |
| 6,852,113 B2 | 2/2005 | Nathanson et al. | |
| 6,890,335 B2 | 5/2005 | Grabowski et al. | |
| 6,932,820 B2 * | 8/2005 | Osman | 606/71 |
| 6,945,973 B2 | 9/2005 | Bray | |
| 6,969,398 B2 * | 11/2005 | Stevens et al. | 606/216 |
| 7,008,427 B2 * | 3/2006 | Sevrain | 606/71 |
| 7,186,254 B2 | 3/2007 | Dinh et al. | |
| 7,201,753 B2 | 4/2007 | Schlapfer et al. | |
| 7,214,226 B2 * | 5/2007 | Alleyne | 606/86 A |
| 7,306,605 B2 | 12/2007 | Ross | |
| 7,318,825 B2 * | 1/2008 | Butler et al. | 606/71 |
| 7,331,961 B2 * | 2/2008 | Abdou | 606/71 |
| 2002/0183754 A1 | 12/2002 | Michelson | |

(Continued)

*Primary Examiner* — Thomas C. Barrett
*Assistant Examiner* — Matthew Lawson (57) ABSTRACT

A bone plate assembly and method of using the same in a patient is disclosed that includes a ratchet mechanism that allows unidirectional incremental adjustment of the overall length of the bone plate assembly. The bone plate assembly is capable of being created to have various stages. One illustrative bone plate assembly includes an intermediate plate component having a first tongue extending upwardly from a central portion of the intermediate plate component and a second tongue extending downwardly from the central portion of the intermediate plate component. First and second end plate components are included that have first and second tongue grooves that are adapted to slidably engage at least a portion of the first and second tongues. A first and second ratchet mechanism is included that allows the first and second end plate components to be incrementally ratcheted toward the central portion of the intermediate plate component.

21 Claims, 9 Drawing Sheets

U.S. PATENT DOCUMENTS

| | | |
|---|---|---|
| 2002/0183755 A1 | 12/2002 | Michelson |
| 2002/0183756 A1 | 12/2002 | Michelson |
| 2002/0183757 A1 | 12/2002 | Michelson |
| 2003/0060828 A1* | 3/2003 | Michelson ................ 606/71 |
| 2003/0149434 A1 | 8/2003 | Paul |
| 2003/0187440 A1 | 10/2003 | Richelsoph et al. |
| 2003/0229348 A1 | 12/2003 | Sevrain |
| 2004/0019353 A1 | 1/2004 | Freid et al. |
| 2004/0092939 A1 | 5/2004 | Freid et al. |
| 2004/0097935 A1 | 5/2004 | Richelsoph et al. |
| 2004/0097938 A1 | 5/2004 | Alleyne |
| 2004/0106924 A1 | 6/2004 | Ralph et al. |
| 2004/0158250 A1 | 8/2004 | Chappuis |
| 2004/0167521 A1 | 8/2004 | De Windt |
| 2004/0181229 A1 | 9/2004 | Michelson |
| 2004/0186476 A1 | 9/2004 | Michelson |
| 2004/0204712 A1 | 10/2004 | Kolb et al. |
| 2004/0204713 A1 | 10/2004 | Abdou |
| 2005/0010227 A1* | 1/2005 | Paul ................ 606/71 |
| 2005/0027297 A1 | 2/2005 | Michelson |
| 2005/0027298 A1 | 2/2005 | Michelson |
| 2005/0043732 A1* | 2/2005 | Dalton ................ 606/61 |
| 2005/0049595 A1 | 3/2005 | Suh et al. |
| 2005/0075633 A1 | 4/2005 | Ross |
| 2005/0085816 A1 | 4/2005 | Michelson |
| 2005/0137597 A1 | 6/2005 | Butler et al. |
| 2005/0149026 A1 | 7/2005 | Butler et al. |
| 2005/0177160 A1 | 8/2005 | Baynham et al. |
| 2005/0187553 A1 | 8/2005 | Grabowski et al. |
| 2005/0192576 A1 | 9/2005 | Michelson |
| 2005/0216009 A1 | 9/2005 | Michelson |
| 2005/0216010 A1 | 9/2005 | Michelson |
| 2005/0216011 A1* | 9/2005 | Paul ................ 606/69 |
| 2005/0240184 A1 | 10/2005 | Osman |
| 2005/0261689 A1 | 11/2005 | Lin |
| 2006/0064097 A1 | 3/2006 | Bray |
| 2006/0079901 A1 | 4/2006 | Ryan et al. |
| 2006/0100625 A1 | 5/2006 | Ralph et al. |
| 2006/0116683 A1* | 6/2006 | Barrall et al. ................ 606/71 |
| 2006/0200134 A1 | 9/2006 | Freid et al. |
| 2006/0217724 A1 | 9/2006 | Suh et al. |
| 2006/0235398 A1* | 10/2006 | Farris et al. ................ 606/69 |
| 2006/0235405 A1* | 10/2006 | Hawkes ................ 606/69 |
| 2006/0271052 A1 | 11/2006 | Stern |
| 2006/0276794 A1 | 12/2006 | Stern |
| 2007/0123881 A1 | 5/2007 | Ralph et al. |
| 2007/0123884 A1 | 5/2007 | Abdou |
| 2007/0162021 A1 | 7/2007 | Dinh et al. |
| 2007/0173851 A1 | 7/2007 | McMillen et al. |
| 2007/0233117 A1 | 10/2007 | Butler et al. |
| 2007/0276371 A1 | 11/2007 | Baynham et al. |
| 2007/0288010 A1 | 12/2007 | Alleyne |
| 2007/0293864 A1 | 12/2007 | Reimels et al. |
| 2008/0015589 A1 | 1/2008 | Hack |
| 2008/0021470 A1 | 1/2008 | Ross |
| 2008/0033438 A1 | 2/2008 | Frizzell |
| 2008/0058810 A1 | 3/2008 | Abdou |
| 2008/0065070 A1 | 3/2008 | Freid et al. |
| 2008/0114361 A1 | 5/2008 | Butler et al. |
| 2008/0269753 A1* | 10/2008 | Cannestra ................ 606/70 |

* cited by examiner

UNI-DIRECTIONAL RATCHETING BONE PLATE ASSEMBLY

TECHNICAL FIELD

The present invention relates generally to the field of surgical instrumentation and methods, and more particularly relates to instrumentation and methods of ratcheting a uni-directional translational bone plate assembly.

BACKGROUND

During anterior fixation or plating of cervical vertebral bodies, the spine is approached from an anterior or anterio-lateral direction and bone screws are used to solidly mount a spinal plate to the affected vertebrae. In some instances, in addition to application of a spinal plate, graft material may be incorporated into the procedure to attempt to permanently fuse together adjacent vertebrae. Frequently, autologous bone, such as that extracted from the ilium, is used as bone graft material, but other bone grafts and devices may also be used.

Fixation of vertebrae is a common approach to treating various types of spinal disorders. In general terms, one or more vertebrae are typically fixed in position relative to one or more other vertebrae. Conventional anterior spinal fixation plates typically include a unitary plate having a pair of bone screw openings at opposite ends. These plates can typically be adjusted bi-directionally, but are sometimes awkward to use, expensive to manufacture, and have larger profiles. The plates may have complex adjustment mechanisms that make adjustment difficult during surgical procedures.

Thus, there remains a need for improved, inexpensive, and easy to use devices and methods for the fixation of vertebrae of the spine.

SUMMARY

A bone plate assembly is disclosed that maintains a low plate profile, is inexpensive, includes a hidden ratchet spring, can be released to allow bi-directional movement, and will not come apart when placed in position. In one embodiment, the bone plate assembly uses a ratchet mechanism that allows one or more end plate components to be moved or ratcheted down to a closed position on an intermediate plate component. In other embodiments, end plate components may be connected together to provide more levels. The ratchet mechanism allows the end components to be incrementally adjusted, preferably in increments of one millimeter, to a desired setting where they are then secured in place. This allows the overall length of the end plate components, in relation to their positioning on the intermediate plate component, to be adjusted thereby allowing the bone plate assembly to be utilized in a variety of patients. The ratchet mechanism only allows the end plate components to move effectively in one direction, which is toward the intermediate plate component.

The intermediate plate component includes tongues that extend outwardly from a central portion of the intermediate plate component. Ratchet springs are located in ratchet spring grooves of the tongues. The end plate components include a tongue groove having a first ratchet spring engagement portion. The tongue grooves are slidably connected with the tongues of the intermediate plate component such that the ratchet springs are in ratcheting engagement with the ratchet spring engagement portions of the end plate components. As used herein, it should be appreciated that the term ratcheting means allowing the end plate components to be incrementally adjusted in one direction on the tongues of the intermediate plate component.

Another aspect of the present invention discloses a method for stabilizing at least two adjacent vertebral bodies in a cervical spine. A bone plate assembly is provided of appropriate length adapted to anteriorly overlap at least a portion of at least two adjacent cervical vertebral bodies. An intermediate plate component of the bone plate assembly may be placed in alignment with a respective vertebra. One or more end plate components, which are connected to the intermediate plate component, may then be adjusted to a proper setting or length to match up with one or more other respective vertebrae. The end plate components are adjusted using a ratchet mechanism included in the bone plate assembly. Once adjusted to the proper length, the bone plate assembly may be secured to the vertebrae of the patient.

Other systems, methods, features and advantages of the invention will be, or will become apparent to one with skill in the art upon examination of the following figures and detailed description. It is intended that all such additional systems, methods, features and advantages be included within this description, be within the scope of the invention, and be protected by the following claims.

BRIEF DESCRIPTION OF THE DRAWINGS

The components in the figures are not necessarily to scale, emphasis instead being placed upon illustrating the principles of the invention. Moreover, in the figures, like reference numerals designate corresponding parts throughout the different views.

DETAILED DESCRIPTION

Figure 1:
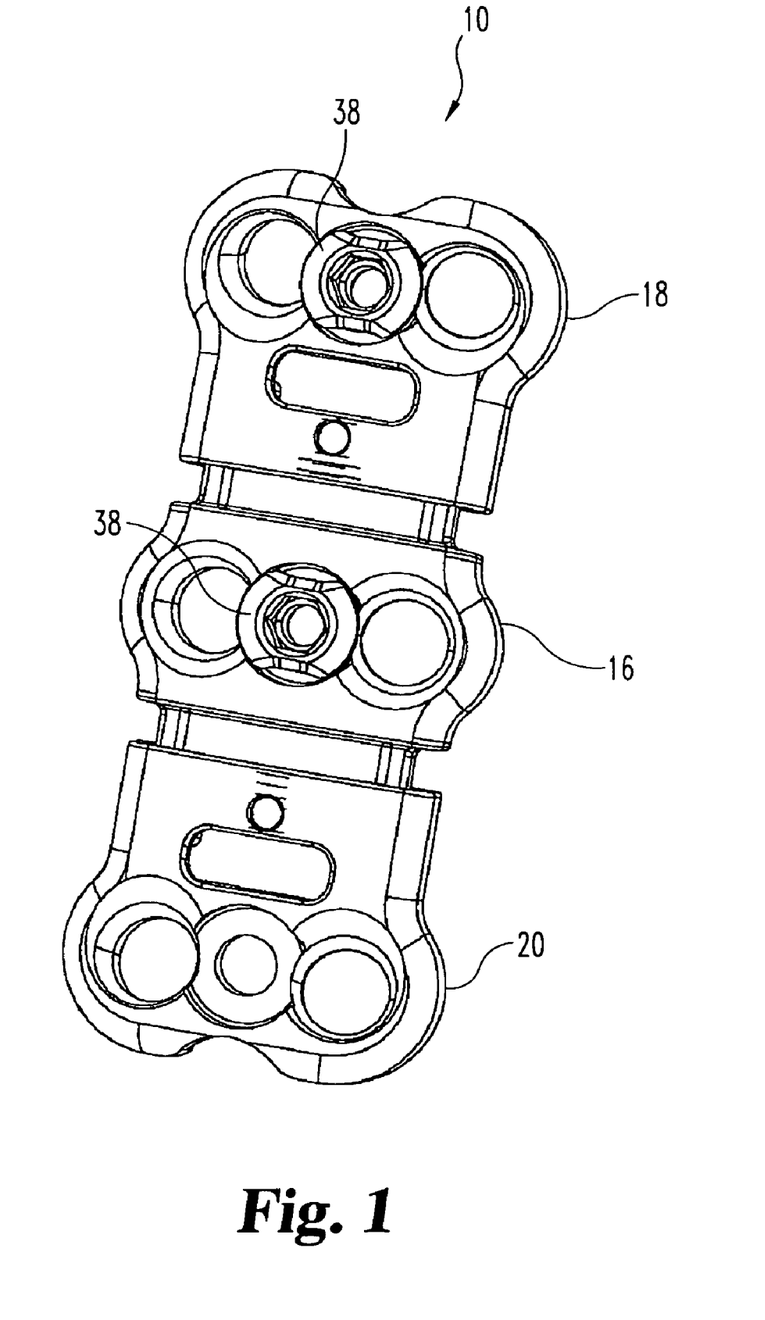
FIG. 1 is a perspective view of a representative bone plate assembly.
Figure 2:
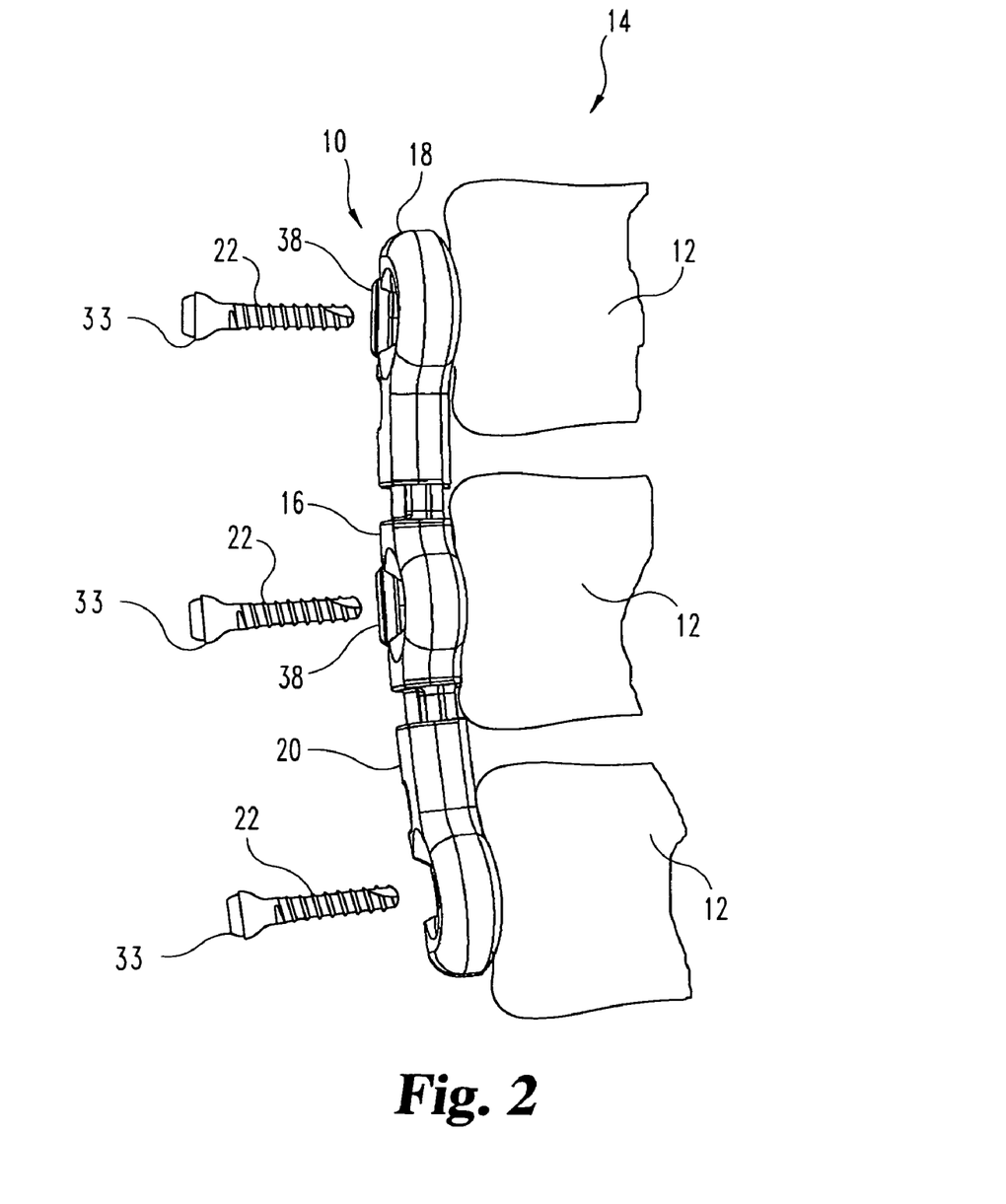
FIG. 2 illustrates the bone plate assembly of FIG. 1 connected with cervical vertebral bodies anteriorly.

Referring to FIGS. 1 and 2, a representative bone plate assembly 10 is illustrated that is operable to be connected to vertebral bodies 12 of a spine 14 to provide alignment and stability. The bone plate assembly 10 may be used as an adjunct to fusion of adjacent vertebral bodies 12 or as an adjunct to other surgical procedures performed on the spine 14. Since the size of vertebral bodies 12 and the spacing between vertebral bodies 12 varies from patient to patient, the bone plate assembly 10 is operable to be incrementally adjusted or ratcheted down to fit various size ranges. Vertebral bodies 12 can be cervical vertebrae or any other vertebrae in any other region of the spine 14, including thoracic, lumbar and sacral regions.

The bone plate assembly 10 includes an intermediate plate component 16, a first end plate component 18 and a second end plate component 20. The first and second end plate components 18, 20 are designed to slide over and ratchet down the intermediate plate component 16. Once the first and second end plates 18, 20, as well as the intermediate plate component 16, are in proper positioning in relation to the vertebral bodies 12 of the spine 14, bone screws 22 may be utilized to secure the bone plate assembly 10 to the vertebral bodies 12. As set forth in more detail below, the end plate components 18, 20 of the bone plate assembly 10 are operable to ratchet down, in a unidirectional manner, in incremental steps of preferably one millimeter until adjusted to the desired or required size.

Figure 3:
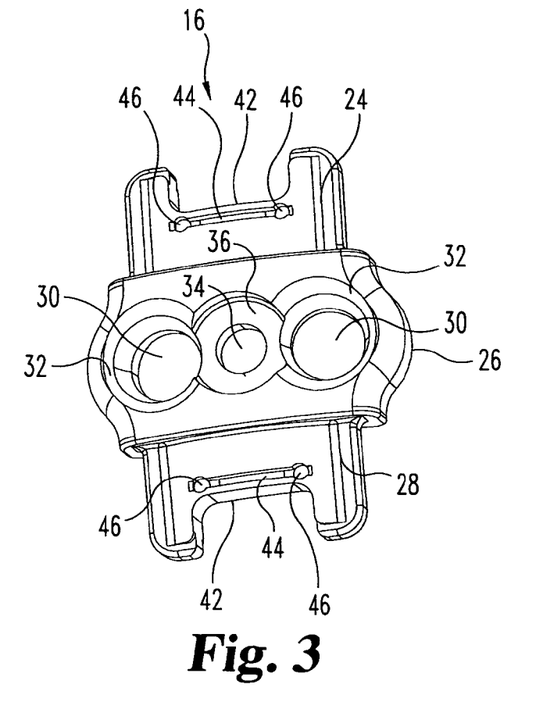
FIG. 3 is a top view of the intermediate plate component of the bone plate assembly.

Referring to FIG. 3, the intermediate plate component 16 has a first tongue 24 that extends upwardly or outwardly from a central portion 26 of the intermediate plate component 16. A second tongue 28 extends downwardly or outwardly, in an opposite direction of the first tongue 24 in the illustrated embodiment, from the central portion 26 of the intermediate plate component 16. The central portion 26 may include a pair of bone screw apertures 30 that hold and receive the bone screws 22. The bone screw apertures 30 may include a spherical recessed portion 32 that allows a spherical head 33 of the bone screws 22 to be recessed in the bone screw apertures 30. A locking cap aperture 34 may also be included in the central portion 26 that may include threads. Another recessed portion 36 may be included around the locking cap aperture 34 so that a locking cap 38 (See FIGS. 1, 8 and 9) may reside in the locking cap aperture 34 in a recessed manner.

Figure 4:
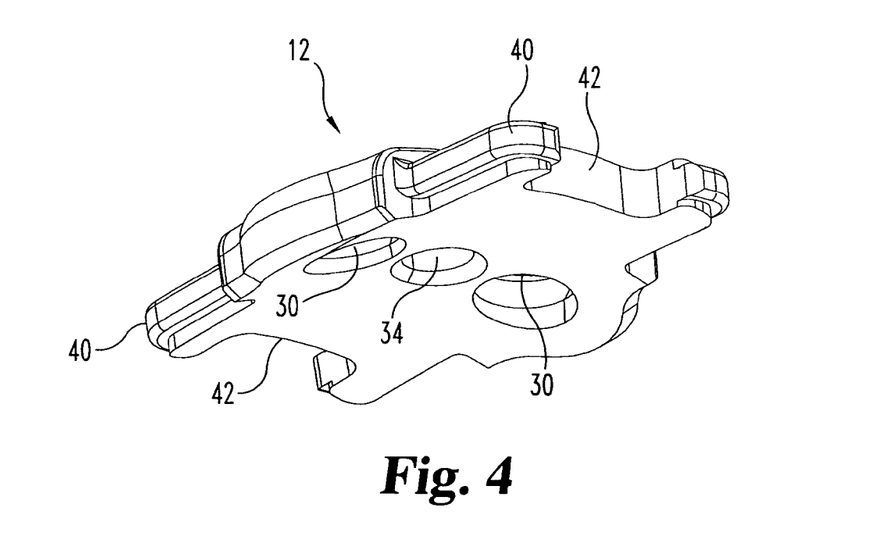
FIG. 4 is a bottom perspective view of the intermediate plate component.

The tongues 24, 28 of the intermediate plate component 16 may have a width somewhat smaller than the width of the central portion 26. As illustrated in FIG. 1, the width of the end caps 18, 20, at least the portion of that is connected to the intermediate plate component 16, may be substantially the same as that of the central portion 26. Referring collectively to FIGS. 3 and 4, the tongues 24, 28 may include a ribbed portion 40 that runs around a portion of the outside perimeter of the tongues 24, 28. In addition, an end of the tongues 24, 28 may include a cutout section 42.

Figure 5:
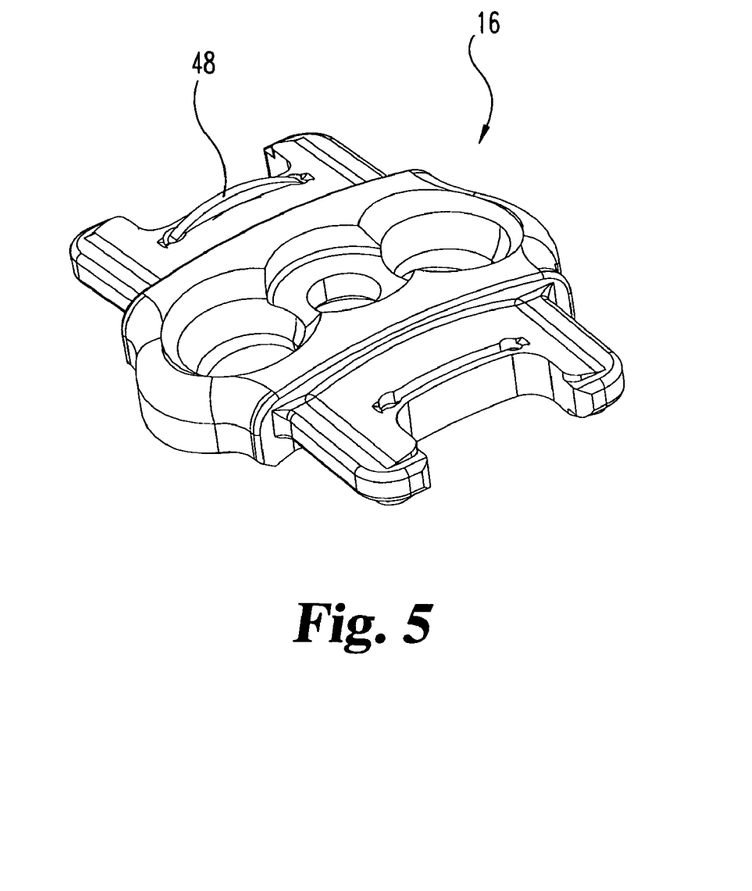
FIG. 5 is a perspective view of the intermediate plate component and a ratchet spring.
Figure 6:
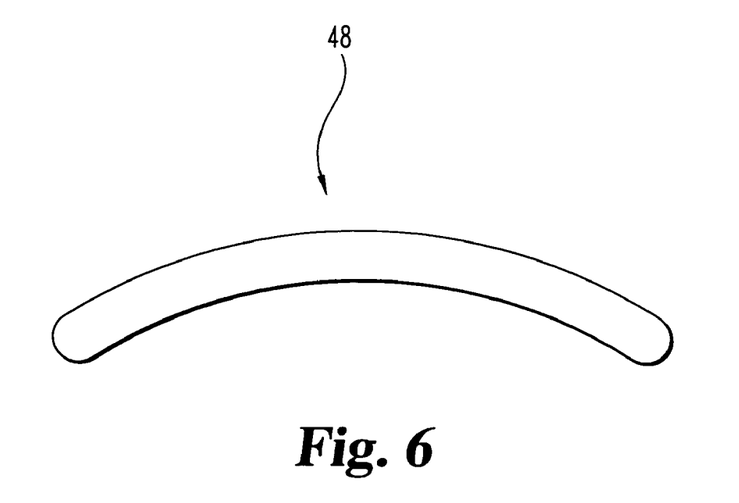
FIG. 6 is a front view of the ratchet spring.

Referring to FIG. 3, the tongues 24, 28 include a ratchet spring notch 44 that runs laterally across the tongues 24, 28. Each ratchet spring notch 44 may include a seat 46 at the ends of the ratchet spring notch 44. As illustrated in FIGS. 5 and 6, each ratchet spring notch 44 holds a ratchet spring 48 that is designed to lock the end plate components 18, 20 to the tongues 24, 28 of the intermediate plate component 16. The ratchet spring 48 is elliptical in shape and may be manufactured from a super-elastic nickel-titanium alloy or other suitable material that naturally tends to maintain its elliptical shape. The ends of the ratchet spring 48 may rest in the seats 46 of the ratchet spring notches 44. When the end plate components 18, 20 are connected with the tongues 24, 28, the ratchet springs 48 are in a depressed state until reaching a ratchet spring notch 58 (See FIG. 8) in the end plate components 18, 20. The ratchet spring 48 then locks the end plate component 18, 20 in the respective position or setting.

Figure 7:
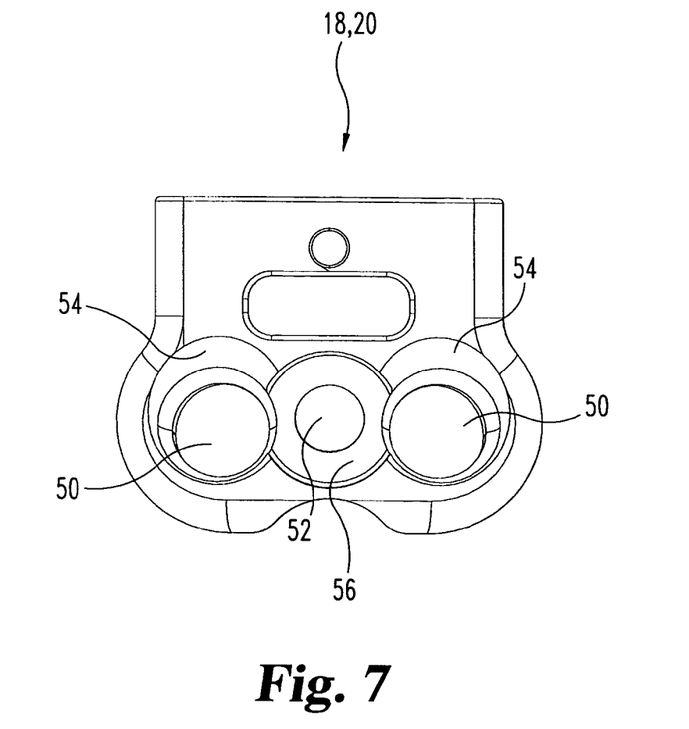
FIG. 7 is a top view of an end plate component.

Referring to FIG. 7, the end plate components 18, 20 may include a pair of bone screw apertures 50 and a locking cap aperture 52. As with the central portion 26 of the intermediate plate component 16, the bone screw apertures 50 may include a spherical recessed portion 54 that allows the spherical heads 33 of the bone screws 22 to be recessed therein. Another recessed portion 56 may be included around the locking cap aperture 34 so that a locking cap 38 may be recessed in the recessed portion 56. All of the bone screw apertures disclosed herein may be sized such that the shaft of the bone screw 22 will pass through the respective aperture while the head of the bone screw 22 will not. This allows the bone screws 22 to securely hold the bone plate assembly 10 to the spine 14 of the patient. The bone screws 22 may be countersunk and locked into place using the locking caps 38, which prevent the bone screws 22 from backing out.

Figure 8:
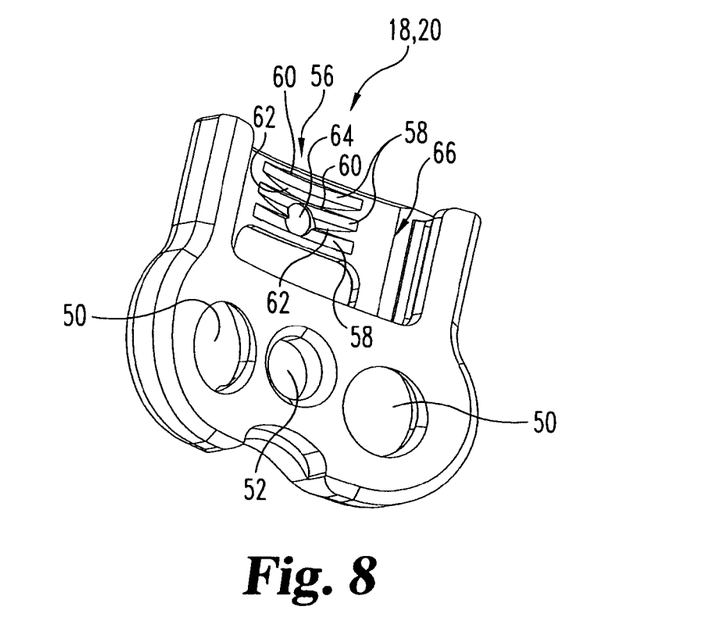
FIG. 8 is a bottom view of the end plate component.

Referring to FIG. 8, the bone plate assembly 10 includes a ratchet mechanism 56 that allows the end plate components 18, 20 to be incrementally ratcheted down toward the central portion 26 of the intermediate plate component 16 in response to compression loading of the vertebrae or in response to applied loading. The bottom of the end plate components 18, 20 include a plurality of ratchet notches 58 that run laterally across a portion of the width of the end plate components 18, 20. The ratchet notches 58 may include a sharp edge portion 60 and a sloped portion 62. The sloped portion 62 has a preferred angle of 30°, but it may vary between 15°-30°. The sharp edge portions 60 keep the end plate components 18, 20 from being able to move away from the intermediate plate component 16 along the tongues 24, 28 in response to tension loading. The sloped portions 62 allow the ratchet springs 48 to move from one setting or ratchet spring notch 58 to another in response to compression loading.

Referring to FIGS. 1, 3, 5 and 8, the ratchet mechanism 56 of the bone plate assembly 10 allows the end plate components 18, 20 to be incrementally adjusted, for instance in one millimeter steps, so that the bone plate assembly 10 can adjust to fit a broad range of vertebral bodies 12 of the spine 14. When a respective end plate component 18, 20 is placed on a tongue 24, 28, the ratchet spring 48 snaps into a respective ratchet spring notch 58 thereby holding the end plate component 18, 20 in place at that particular setting. If the length of the bone plate assembly 10 needs to be adjusted, pressure may be applied to the end of a respective end plate component 18, 20 which, once enough pressure is applied, will cause the ratchet spring 48 to move down the slope portion 62 into another ratchet spring notch 58. In another embodiment, a ratchet spring aperture 64 may be included that exposes a portion of the ratchet spring 48 thereby allowing an instrument to be inserted to apply downward force on the ratchet spring 48. This downward force may release the ratchet spring 48 from a respective ratchet spring notch 58 thereby allowing bi-directional adjustment.

Figure 9:
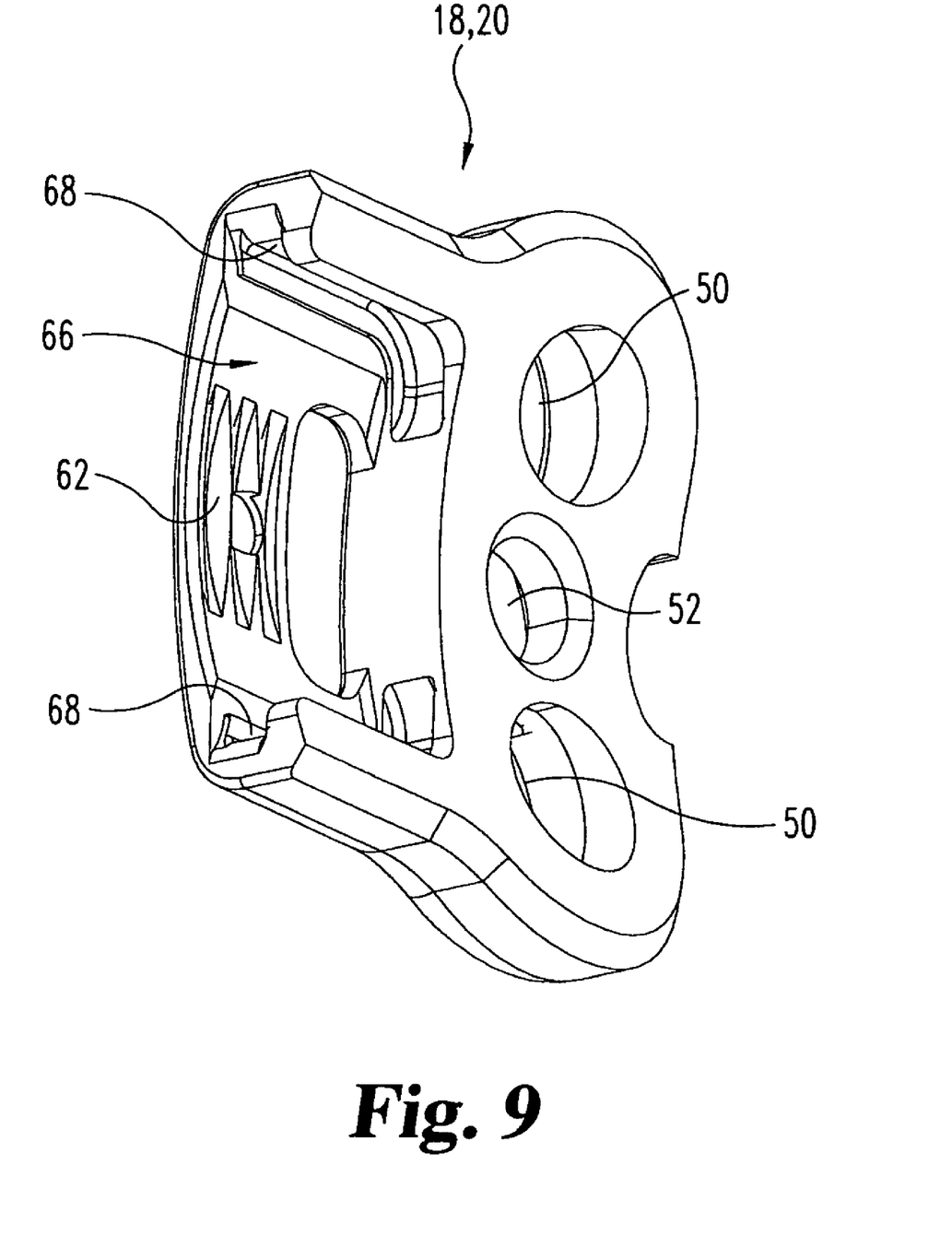
FIG. 9 is another bottom view of the end plate component.

Referring to FIGS. 8 and 9, the end plate components 18, 20 include a groove portion 66 that is shaped to fit or slide over the tongues 24, 28 of the intermediate plate component 16. As such, the end plate components 18, 20 are secured to the intermediate plate component 16 in a tongue and groove manner or arrangement. The groove portion 66 of the end plate components 18, 20 may include U-shaped securing cutouts 68. The ribbed portion 40 of the tongues 18, 20 fit within the U-shaped securing cutouts 68 thereby securing the end plate components 18, 20 to the intermediate plate component 16.

Figure 10:
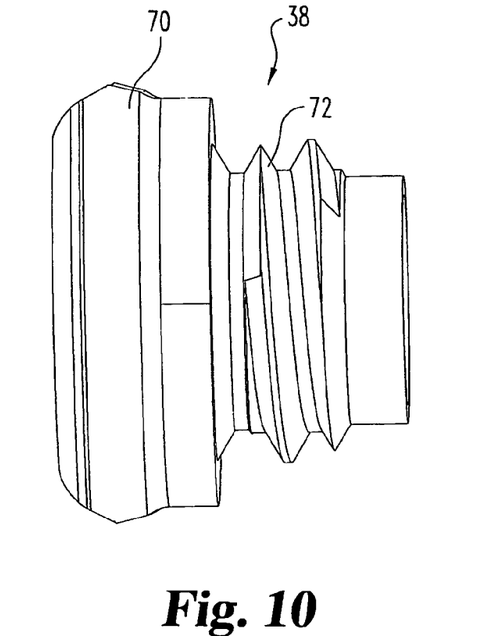
FIG. 10 is a side view of a locking cap.
Figure 11:
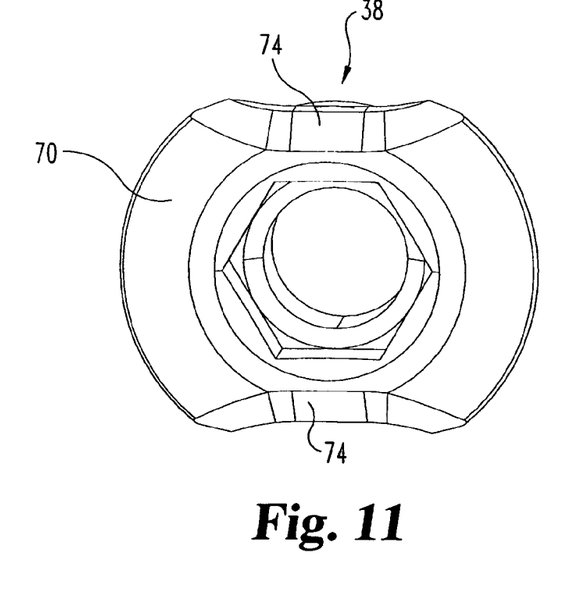
FIG. 11 is a top view of a locking cap.

Referring to FIGS. 1, 10 and 11, the bone plate assembly may also include a plurality of locking caps 38. The locking caps 38 are connected to the locking cap aperture 34 of the intermediate plate component 16 and the locking cap apertures 52 of the end plate components 18, 20. The locking caps 38 may include a head portion 70 and a threaded portion 72. The head portion 70 is partially circular in shape but contains two recessed cutouts 74 on opposing sides. As partially illustrated in FIG. 1, once the bone screws 22 are in place, the locking caps 38 may be turned such that the recessed cutouts 74 are not in alignment with the bone screw apertures 30, 50.

As such, a portion of the head portion 70 of the locking caps 38 covers a portion of the head 33 of the bone screw 22. The two recessed cutouts 74 provide sufficient space such that when they are aligned with the bone screw apertures 30, 50, the heads 33 of the bone screws 22 are capable of being placed in a countersunk position, as previously set forth.

Another aspect of the present invention discloses a method for stabilizing at least two adjacent vertebral bodies 12 in a cervical spine 14. A bone plate assembly 10 is provided of appropriate length adapted to overlap at least a portion of at least two adjacent cervical vertebral bodies 12 anteriorly. The bone plate assembly 10 includes an intermediate plate component 16 having a first end plate component 18 engaged by a first ratchet mechanism 56 with a first tongue 24 of the intermediate plate component 16. A second end plate component 20 is engaged by a second ratchet mechanism 56 with a second tongue 28 of the intermediate plate component 16.

A first length of the first end plate component 18 in relation to the intermediate plate component 16 may be adjusted using the first ratchet mechanism 56 such that a first bone screw aperture 50 of the first end plate component 18 is in alignment with at least a portion of a first cervical vertebral body 12. A second length of the second end plate component 20 in relation to the intermediate plate component 16 may be adjusted using the second ratchet mechanism 56 such that a second bone screw aperture 50 of the second end plate component 20 is in alignment with at least a portion of a second cervical vertebral body 12. A first bone screw 22 is inserted through the first bone screw aperture 50 into the first cervical vertebral body 12 thereby securing the bone plate assembly 10 to the first cervical vertebral body 12. A second bone screw 22 is inserted through the second bone screw aperture 50 into the second cervical vertebral body 12 thereby securing the bone plate assembly 10 to the second cervical vertebral body 12.

Figure 12:
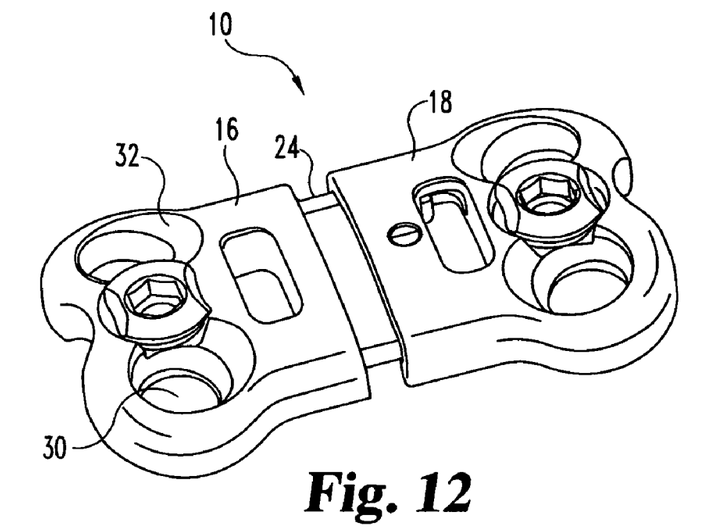
FIG. 12 is a perspective view of a one-stage bone plate assembly.

Referring to FIG. 12, in another embodiment of the present invention, only one end plate component 18 is utilized in the bone plate assembly 10. As such, only one tongue 24 slidably engages the end plate component 18. The second tongue 28 may be eliminated and the central portion 26 may be shaped as illustrated. The ratchet mechanism 56 remains the same as that described in connection with the other embodiments. This embodiment is also applicable to the method disclosed herein in that only one end plate component 18 needs to be aligned with a respective vertebra 12. The bone plate assembly 10 illustrated in FIG. 12 would be referred to as a one-stage bone plate assembly 10.

Figure 13:
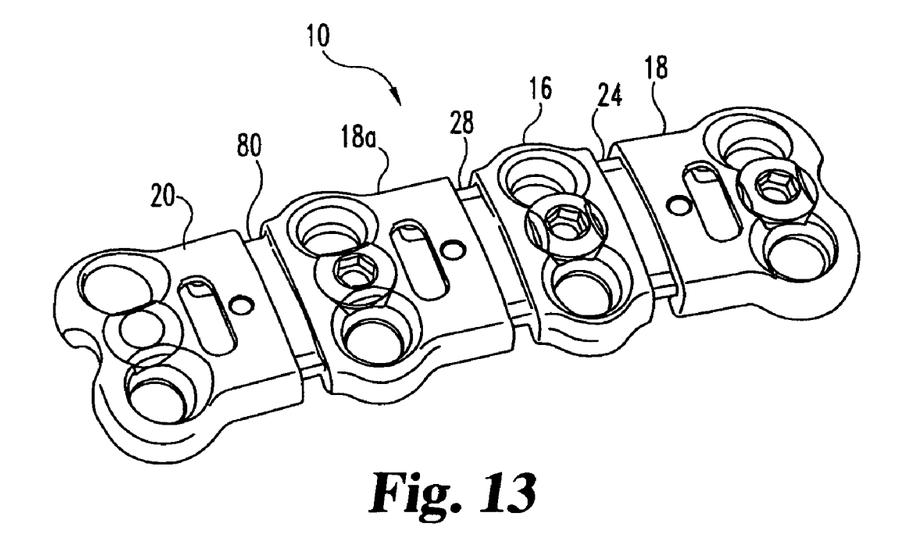
FIG. 13 is a perspective view of a three-stage bone plate assembly.

Referring to FIG. 13, a three-stage bone plate assembly 10 is illustrated. In this embodiment, an intermediate plate component 16 is included that has the same features as described in relation to FIGS. 1, 3, 4 and 5. A first end plate component 18 includes a groove portion 66 that is shaped to fit or slide over a first tongue 24 of the intermediate plate component 16. An expansion end plate component 18a also includes a groove portion 66 that is shaped to fit or slide over a second tongue 28 of the intermediate plate component 16. In this embodiment, an opposing end of the expansion end plate component 18a includes a tongue portion 80. As illustrated, a second end plate component 20 may be connected with the tongue portion 80 of the expansion end plate component 18a. As such, in this embodiment, the end plate component 18, the expansion end plate component 18a, and the second end plate component 20 may all be incrementally adjusted the same as described in relation to the embodiment illustrated in FIG. 1.

Figure 14:
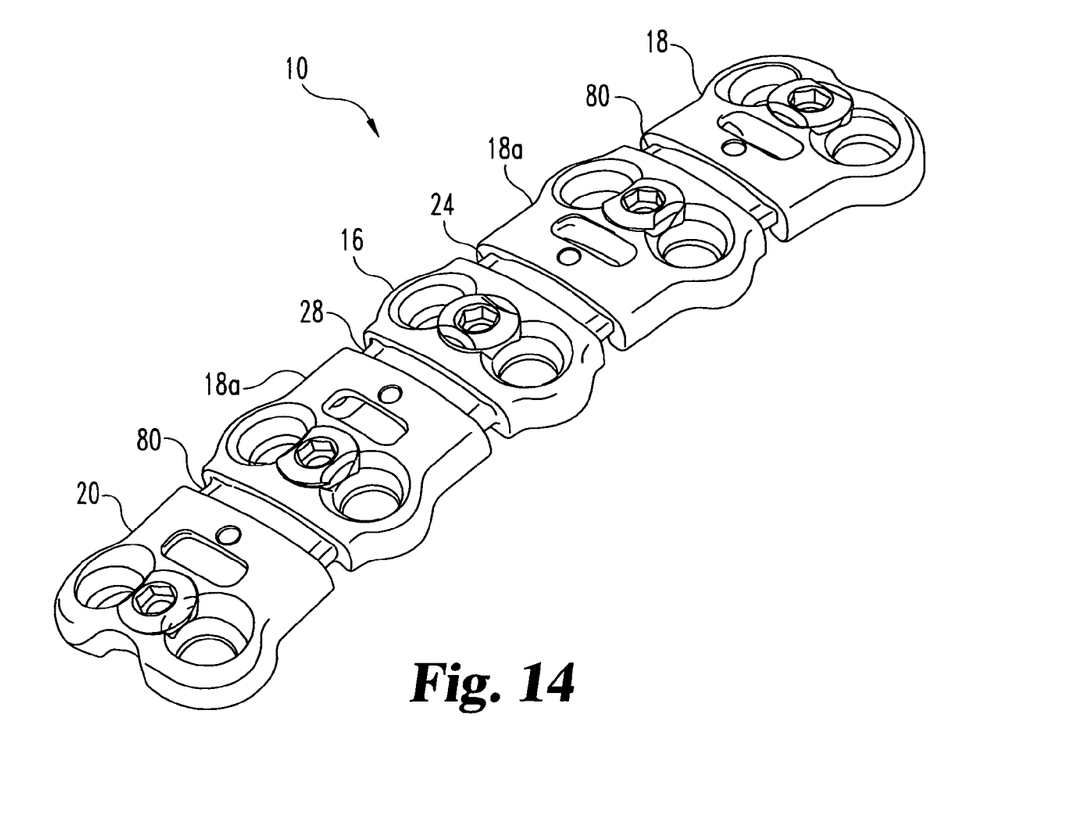
FIG. 14 is a perspective view of a four-stage bone plate assembly.

Referring to FIG. 14, a four-stage bone plate assembly 10 is illustrated. In this embodiment, two expansion end plate components 18a are utilized. Each expansion end plate component 18a is connected with a respective tongue 24, 28 of the intermediate plate component 16. As with the embodiment described with respect to FIG. 13, each expansion end plate component 18a includes a tongue portion 80. First and second end plate components 18, 20 are capable of sliding over the tongue portions 80 thereby creating four incrementally adjustable stages. The remaining features of this embodiment operate the same as that described with respect to FIG. 1. Those skilled in the art would recognize and appreciate that other stage combinations, such as a five-stage bone plate assembly, may be created using the principles of the present invention.

While the invention has been illustrated and described in detail in the drawings and foregoing description, the same is to be considered as illustrative and not restrictive in character.

What is claimed is:

1. A bone plate assembly, comprising:
an intermediate plate component having a first and second tongue portion extending outwardly from a central portion;
a first ratchet spring positioned in a ratchet spring groove of said first tongue portion and a second ratchet spring positioned in a second ratchet spring groove of said second tongue portion, wherein said ratchet spring grooves each include seats located at opposite ends thereof and said first ratchet spring includes opposite ends positioned in respective ones of said seats of said ratchet spring groove of said first tongue portion and said second ratchet spring includes opposite ends positioned in respective ones of said seats of said ratchet spring groove of said second tongue portion; and
a first end plate component including a first tongue groove portion having a first ratchet spring engagement portion and a second end plate component including a second tongue groove portion having a second ratchet spring engagement portion, wherein said first and second tongue groove portions are slidably connected with said first and second tongue portions of said intermediate plate component such that said first and second ratchet springs are in ratcheting engagement with said first and second ratchet spring engagement portions, wherein said first and second ratchet spring engagement portions comprise a plurality of spaced lateral notches cut into an underside surface of said respective first and second tongue groove portions and said first and second ratchet springs are elliptically bowed outwardly from a respective one of said ratchet spring grooves into an aligned one of said plurality of spaced lateral notches.

2. The bone plate assembly of claim 1, wherein between said plurality of spaced lateral notches is a sloped portion that allows said first and second ratchet springs to ratchet between said plurality of spaced lateral notches.

3. The bone plate assembly of claim 1, wherein said first and second end plate components include at least one bone screw receiving aperture.

4. The bone plate assembly of claim 3, wherein said at least one bone screw receiving aperture includes a recessed upper portion such that a head of a respective bone screw is countersunk in said at least one bone screw receiving aperture.

5. The bone plate assembly of claim 4, further comprising a locking cap aperture located at a central portion of said first and second end plate components.

6. The bone plate assembly of claim 5, further comprising a locking cap positioned in said locking cap aperture such that a portion of said locking cap is operable to cover a portion of said head of said respective bone screw thereby locking said respective bone screw in a set position.

7. The bone plate assembly of claim 1, wherein said intermediate plate component includes at least one bone screw receiving aperture.

8. The bone plate assembly of claim 7, wherein said at least one bone screw receiving aperture includes a recessed upper portion such that a head of a respective bone screw is countersunk in said at least one bone screw receiving aperture.

9. The bone plate assembly of claim 8, further comprising a locking cap positioned in said locking cap aperture such that a portion of said locking cap is operable to cover a portion of said head of said respective bone screw thereby locking said respective bone screw in a set position.

10. The bone plate assembly of claim 1, wherein said first and second ratchet spring engagement portions include a ratchet spring access aperture.

11. The vertebral body bone plate assembly of claim 10, wherein a portion of said first and second ratchet springs are accessible from said respective ratchet spring access apertures such that application of downward force on said first and second ratchet springs causes said end plate components to release thereby allowing bidirectional movement of said first and second end plate components on said first and second tongues.

12. A bone plate assembly, comprising:
an intermediate plate component having a tongue extending outwardly from a central portion of said intermediate plate component;
an end plate component having a tongue groove adapted to slidably engage at least a portion of said tongue and a ratchet spring engagement portion; and
a ratchet mechanism engaged to said tongue allowing said end plate component to be incrementally ratcheted toward said central portion of said intermediate plate component, wherein said tongue groove is slidably connected with said tongue of said intermediate plate component such that said ratchet mechanism is in ratcheting engagement with ratchet spring engagement portion along said tongue groove, wherein said ratchet spring engagement portion comprises a plurality of spaced notches in an underside surface of said tongue groove, wherein said tongue of said intermediate plate component includes a ratchet spring groove with seats located at opposite ends thereof and said ratchet mechanism includes a ratchet spring with opposite tongue and said ratchet spring is bowed outwardly from said ratchet spring groove into an aligned one of said plurality of spaced lateral notches.

13. The bone plate assembly of claim 12, wherein said ratchet spring is operable to engage a respective one of a plurality of spaced ratchet spring notches in said end plate component.

14. The bone plate assembly of claim 13, further comprising a sloped section between each of said respective spaced ratchet spring notches.

15. The bone plate assembly of claim 12, wherein said end plate component includes at least one bone screw receiving aperture.

16. The bone plate assembly of claim 12, wherein said intermediate plate component includes at least one bone screw receiving aperture.

17. The bone plate assembly of claim 12, wherein said end plate component includes a locking cap for preventing a bone screw from backing out of a bone screw aperture in said end plate component.

18. The bone plate assembly of claim 12, wherein said tongue groove of said end plate components includes a U-shaped engagement portion that slidably engages a ribbed portion of said tongue.

19. A bone plate assembly, comprising:
an intermediate plate component having a tongue extending outwardly from a central portion;
a ratchet spring positioned in a ratchet spring groove of said tongue; and
an end plate component including a tongue groove portion having a ratchet spring engagement portion, wherein said tongue groove portion is slidably connected with said tongue of said intermediate plate component such that said ratchet spring is in ratcheting engagement with said ratchet spring engagement portion, wherein said ratchet spring engagement portion comprises a plurality of spaced notches in an underside surface of said tongue groove portion wherein said ratchet spring groove of said tongue of said intermediate plate component includes seats located at opposite ends thereof and said ratchet spring includes opposite ends positioned in respective ones of said seats of said ratchet spring groove of said tongue and said ratchet spring is bowed outwardly from said ratchet spring groove into an aligned one of said plurality of spaced lateral notches.

20. A bone plate assembly, comprising:
an intermediate plate component having a first and second tongue portion extending outwardly from a central portion;
a first ratchet spring positioned in a ratchet spring groove of said first tongue portion and a second ratchet spring positioned in a second ratchet spring groove of said second tongue portion, wherein said ratchet spring grooves each include seats located at opposite ends thereof and said first ratchet spring includes opposite ends positioned in respective ones of said seats of said ratchet spring groove of said first tongue portion and said second ratchet spring includes opposite ends positioned in respective ones of said seats of said ratchet spring groove of said second tongue portion;
an expansion end plate component including a first tongue groove portion having a first ratchet spring engagement portion and a third tongue portion, wherein a third ratchet spring is positioned in a ratchet spring groove of said third tongue portion and said ratchet spring groove of said third tongue portion includes seats located at opposite ends thereof and said third ratchet spring includes opposite ends positioned in said seats of said ratchet spring groove of said third tongue portion, wherein said first tongue groove portion is slidably connected with said first tongue portion of said intermediate plate component such that said first ratchet spring is in ratcheting engagement with said first ratchet spring engagement portion; and
a first end plate component including a second tongue groove portion having a second ratchet spring engagement portion and a second end plate component including a third tongue groove portion having a third ratchet spring engagement portion, wherein said second tongue groove portion of said first end plate component is slidably connected with said second tongue portion of said intermediate plate component such that said second ratchet spring is in ratcheting engagement with said second ratchet spring engagement portion, and wherein said third tongue groove portion of said second end plate component is slidably connected with said third tongue portion of said expansion end plate component such that said third ratchet spring is in ratcheting engagement with said first ratchet spring engagement portion, wherein said first, second and third ratchet spring engagement portions each comprise a plurality of spaced lateral notches cut into an underside surface of said respective first, second and third tongue groove portions and said first, second and third ratchet springs are bowed outwardly from a respective one of said ratchet spring grooves into an aligned one of said plurality of spaced lateral notches of a respective one of said first, second and third ratchet spring engagement portions.

21. A bone plate assembly, comprising:

an intermediate plate component having a first and second tongue portion extending outwardly from a central portion;

a first ratchet spring positioned in a ratchet spring groove of said first tongue portion and a second ratchet spring positioned in a second ratchet spring groove of said second tongue portion, wherein said ratchet spring grooves each include seats located at opposite ends thereof and said first ratchet spring includes opposite ends positioned in respective ones of said seats of said ratchet spring groove of said first tongue portion and said second ratchet spring includes opposite ends positioned in respective ones of said seats of said ratchet spring groove of said second tongue portion;

a first expansion end plate component including a first tongue groove portion having a first ratchet spring engagement portion and a third tongue portion and a second expansion end plate component including a second tongue groove portion having a second ratchet spring engagement portion, wherein a third ratchet spring is positioned in a ratchet spring groove of said third tongue portion and a fourth ratchet spring is positioned in a ratchet spring groove of said fourth tongue portion, wherein said ratchet spring grooves of said first and second expansion end plate components each include seats located at opposite ends thereof and said third ratchet spring includes opposite ends positioned in respective ones of said seats of said ratchet spring groove of said first tongue groove portion and said fourth ratchet spring includes opposite ends positioned in respective ones of said seats of said ratchet spring groove of said second tongue groove portion, wherein said first tongue groove portion is slidably connected with said first tongue portion of said intermediate plate component such that said first ratchet spring is in ratcheting engagement with said first ratchet spring engagement portion and said second tongue groove portion is slidably connected with said second tongue portion of said intermediate plate component such that said second ratchet spring is in ratcheting engagement with said second ratchet spring engagement portion, wherein said first and second ratchet spring engagement portions of said first and second expansion end plate components comprise a plurality of spaced lateral notches cut into an underside surface of said respective first and second tongue groove portions and said first and second springs are bowed outwardly from a respective one of said ratchet spring grooves of said first and second tongue groove portions into an aligned one of said plurality of spaced lateral notches of said first and second ratchet spring engagement portions; and a first end plate component including a third tongue groove portion having a third ratchet spring engagement portion and a second end plate component including a fourth tongue groove portion having a fourth ratchet spring engagement portion, wherein said third tongue groove portion of said first end plate component is slidably connected with said third tongue portion of said first expansion end plate component such that said third ratchet spring is in ratcheting engagement with said third ratchet spring engagement portion, and wherein said fourth tongue groove portion of said second end plate component is slidably connected with said fourth tongue portion of said second expansion end plate component such that said fourth ratchet spring is in ratcheting engagement with said fourth ratchet spring engagement portion wherein said third and fourth ratchet spring engagement portions each comprise a plurality of spaced lateral notches cut into an underside surface of said respective third and fourth tongue groove portions and said third and fourth ratchet springs are bowed outwardly from a respective one of said ratchet spring grooves into an aligned one of said plurality of spaced lateral notches of said third and fourth ratchet spring engagement portions.

\* \* \* \* \*